(12) United States Patent
Hares

(10) Patent No.: US 9,943,964 B2
(45) Date of Patent: Apr. 17, 2018

(54) CHARACTERISING ROBOT ENVIRONMENTS

(71) Applicant: CAMBRIDGE MEDICAL ROBOTICS LIMITED, Cambridge (GB)

(72) Inventor: Luke David Ronald Hares, Cambridge (GB)

(73) Assignee: CMR SURGICAL LIMITED, Cambridge, MA (US)

( * ) Notice: Subject to any disclaimer, the term of this patent is extended or adjusted under 35 U.S.C. 154(b) by 1 day.

(21) Appl. No.: 15/166,449

(22) Filed: May 27, 2016

(65) Prior Publication Data

US 2016/0346930 A1 Dec. 1, 2016

(30) Foreign Application Priority Data

May 29, 2015 (GB) .................................. 1509341.2

(51) Int. Cl.
*B25J 9/00* (2006.01)
*B25J 9/16* (2006.01)
(Continued)

(52) U.S. Cl.
CPC ............. *B25J 9/1692* (2013.01); *A61B 34/30* (2016.02); *A61B 34/32* (2016.02); *B25J 9/1679* (2013.01);
(Continued)

(58) Field of Classification Search
USPC ......... 700/245–264; 318/567–568.25; 901/6, 901/46, 50
See application file for complete search history.

(56) References Cited

U.S. PATENT DOCUMENTS

| 4,894,908 A | * | 1/1990 | Haba, Jr. ............... B23P 21/004 29/711 |
| 5,333,242 A | | 7/1994 | Watanabe et al. |

(Continued)

FOREIGN PATENT DOCUMENTS

| WO | 2014042668 A2 | 3/2014 |
| WO | 2014148032 A1 | 9/2014 |

OTHER PUBLICATIONS

International Search Report from corresponding PCT/GB2016/051557 dated Sep. 30, 2016.
(Continued)

*Primary Examiner* — Jonathan L Sample
(74) *Attorney, Agent, or Firm* — Lando & Anastasi, LLP

(57) ABSTRACT

A method for characterizing the environment of a robot, the robot having a flexible arm having a plurality of joints, a datum carried by the arm, a plurality of drivers arranged to drive the joints to move and a plurality of position sensors for sensing the position of each of the joints, the method comprising: contacting the datum carried by the arm with a first datum on a second robot in the environment of the first robot, wherein the second robot has a flexible arm having a plurality of joints, and a plurality of drivers arranged to drive those joints to move; calculating in dependence on the outputs of the position sensors a distance between a reference location defined in a frame of reference local to the robot and the first datum; and controlling the drivers to reconfigure the first arm in dependence on at least the calculated distance.

19 Claims, 7 Drawing Sheets

(51) Int. Cl.
*A61B 34/30* (2016.01)
*A61B 34/32* (2016.01)

(52) U.S. Cl.
CPC ... *B25J 9/1682* (2013.01); *G05B 2219/39021* (2013.01); *G05B 2219/39024* (2013.01); *G05B 2219/39026* (2013.01); *G05B 2219/39047* (2013.01); *G05B 2219/39051* (2013.01); *G05B 2219/39135* (2013.01); *G05B 2219/39399* (2013.01)

(56) References Cited

U.S. PATENT DOCUMENTS

| | | | |
|---|---|---|---|
| 5,929,584 A | 7/1999 | Gunnarsson et al. | |
| 6,175,206 B1* | 1/2001 | Ueno | B25J 9/1658 318/568.1 |
| 6,594,550 B1* | 7/2003 | Okrah | B25J 9/1656 318/563 |
| 6,804,580 B1* | 10/2004 | Stoddard | B25J 9/1669 318/568.1 |
| 6,807,461 B2* | 10/2004 | Kneifel, II | B25J 9/1682 118/500 |
| 7,010,390 B2 | 3/2006 | Graf et al. | |
| 7,096,090 B1* | 8/2006 | Zweig | G05D 1/0022 700/245 |
| 7,643,907 B2* | 1/2010 | Fuhlbrigge | B25J 9/1656 700/245 |
| 7,650,205 B2* | 1/2010 | Calcagno | G05B 19/42 318/568.1 |
| 7,783,387 B2* | 8/2010 | Calcagno | G05B 19/42 318/567 |
| 8,073,567 B2* | 12/2011 | Nishi | G05B 19/41815 318/568.14 |
| 8,200,796 B1* | 6/2012 | Margulis | G06F 3/1431 709/217 |
| 8,793,018 B2* | 7/2014 | Muller | H04L 12/40163 700/247 |
| 9,102,060 B2* | 8/2015 | Tarragona | B25J 9/1656 |
| 9,283,678 B2* | 3/2016 | Kuffner, Jr. | B25J 9/1676 |
| 9,632,493 B2* | 4/2017 | Negre | G05B 19/0426 |
| 9,643,314 B2* | 5/2017 | Guerin | B25J 9/1605 |
| 9,778,646 B2* | 10/2017 | Ikeda | G05B 19/402 |
| 2001/0004718 A1* | 6/2001 | Gilliland | B25J 9/1671 700/255 |
| 2003/0070025 A1* | 4/2003 | Watts | G06F 13/4291 710/305 |
| 2005/0225278 A1 | 10/2005 | Ban et al. | |
| 2005/0273199 A1* | 12/2005 | Ban | B25J 9/1682 700/248 |
| 2006/0271209 A1* | 11/2006 | Calcagno | G05B 19/42 700/19 |
| 2007/0061041 A1* | 3/2007 | Zweig | G05D 1/0261 700/245 |
| 2007/0299557 A1 | 12/2007 | Watanabe et al. | |
| 2008/0114492 A1* | 5/2008 | Miegel | B25J 9/1664 700/248 |
| 2008/0263628 A1* | 10/2008 | Norman | G08C 17/02 726/1 |
| 2008/0300723 A1 | 12/2008 | Ban et al. | |
| 2009/0198370 A1* | 8/2009 | Nishi | G05B 19/41815 700/184 |
| 2010/0017033 A1* | 1/2010 | Boca | B25J 9/0093 700/258 |
| 2010/0063625 A1* | 3/2010 | Krause | G05B 19/4182 700/245 |
| 2010/0161125 A1 | 6/2010 | Aoba et al. | |
| 2010/0325623 A1* | 12/2010 | Ikeda | B25J 9/1656 717/173 |
| 2011/0098854 A1* | 4/2011 | Tarragona | B25J 9/1656 700/245 |
| 2014/0277715 A1 | 9/2014 | Nagai et al. | |
| 2014/0277722 A1 | 9/2014 | Nagai et al. | |
| 2014/0324070 A1* | 10/2014 | Min | A61B 34/30 606/130 |

OTHER PUBLICATIONS

United Kingdom Search Report from corresponding United Kingdom Application No. GB1509341.2 dated Dec. 11, 2015.

* cited by examiner

CHARACTERISING ROBOT ENVIRONMENTS

CROSS-REFERENCE TO RELATED APPLICATION

This application claims the benefit under 35 U.S.C. § 119 of United Kingdom Patent Application No. 1509341.2 filed on May 29, 2015 which is hereby incorporated herein by reference in its entirety for all purposes.

BACKGROUND OF THE INVENTION

This invention relates to characterising the spatial relationships of objects around robots, for example surgical robots.

Some surgical robots are of considerable bulk and comprise multiple surgical arms stemming from a single fixed or mobile base. In these systems the fact that the surgical arms are mechanically attached to a common base means that the spatial relationship between the arms is inherent and can readily be established through knowledge of the arms' configurations. However, these systems are bulky, making them difficult to move into place in an operating theatre. Also, the range of possible spatial relationships between the arms is limited by the fact that the arms stem from a single base, and this restricts the range of surgical procedures that can be carried out by such systems.

FIG. 1 illustrates three separate surgical robots 1, 2, 3 each having a respective arm. The robots are positioned in preparation for performing surgery on a patient 4 who is on an operating table 5. The robots are communicatively linked to a control station 7 from where they can be operated by a surgeon. In this example robot 3 is fixedly mounted to the ceiling of the operating theatre. Robots 1 and 2 are mounted on mobile carts 8, 9. The carts are equipped with lockable wheels so that they can be pushed into place by a technician before surgery begins and then fixed in place for the duration of the operation. The table on which the patient lies is also on lockable wheels. The patient can be prepared for surgery outside the theatre and then moved into the operating theatre on the table. This flexibility of positioning of the patient and the robots has the advantage that the equipment can perform a greater range of procedures than some other robot systems. However, it has the consequence that after the table and the carts 8, 9 have been moved into place the relative positions of the bases of the arms 1, 2, 3 are essentially unknown, as is their relationship to the table 5 on which the patient is resting.

The spatial relationships between the arms would be useful information for the control station 7. It could, for example, be used to avoid collisions between the arms.

One way to establish the spatial relationships between the arms would be to provide a set of jigs or floor markings that are used by the technician to set the positions of the robots' carts and/or the patient's table. The spatial relationships between the apparatus would then be known. However, very many such jigs or markings would be needed to provide for the full range of surgical procedures.

Another way to establish the spatial relationships would be for the technician to measure the distances between datum points on the arms and the table and to input that data to the control system. This is time-consuming because to fully characterise the spatial relationships in three dimensions many such measurements would be needed, and there is the possibility that errors might be made in taking the measurements or entering them in.

There is a need for an alternative way of establishing the spatial relationship between robots, particularly surgical robots.

BRIEF SUMMARY OF THE INVENTION

According to the present invention there is provided a method for characterising the environment of a robot, the robot having a base, a flexible arm extending from the base and having a plurality of joints whereby the configuration of the arm can be altered, a datum carried by the arm, a plurality of drivers arranged to drive the joints to move and a plurality of position sensors for sensing the position of each of the joints, the method comprising: contacting the datum carried by the arm with a first datum on an object in the environment of the robot; calculating in dependence on the outputs of the position sensors a distance between a reference location defined in a frame of reference local to the robot and the first object datum; and controlling the drivers to reconfigure the arm in dependence on at least the calculated distance.

The method may comprise contacting the datum carried by the arm with a second datum on the object; calculating in dependence on the outputs of the position sensors when the datum carried by the arm is contacted with the first object datum and with the second object datum an orientation of the object relative to a reference direction defined in a frame of reference local to the robot; and controlling the drivers to reconfigure the arm in dependence on at least the calculated orientation The method may comprise mating the datum carried by the arm with a datum on the object, the arm datum and the object datum being mutually configured so that the configuration of the arm is dependent on the orientation of the object when the arm datum and the object datum are mated; calculating in dependence on the outputs of the position sensors when the arm datum and the object datum are mated an orientation of the object relative to a reference direction defined in a frame of reference local to the robot; and controlling the drivers to reconfigure the arm in dependence on at least the calculated orientation.

The or each step of calculating may be performed in dependence on stored information defining the lengths of the parts of the arm separated by the joints.

The or each step of controlling may be performed in dependence on stored information defining the shape of the object.

The robot may be a surgical robot.

The object may be an operating table or another article of surgical furniture.

The step of controlling the drivers to reconfigure the arm in dependence on the calculated distance and/or orientation may comprise controlling the drivers so as to inhibit collision between the or each arm and the object in dependence on the calculated distance and/or orientation.

The object may be a second robot.

The second robot may have a base, a flexible arm extending from the base and having a plurality of joints whereby the configuration of the arm can be altered, and a plurality of drivers arranged to drive those joints to move, the method comprising: controlling the drivers of the second robot to reconfigure the arm of the second robot in dependence on the calculated distance and/or orientation.

The or each robot may be mounted on a movable cart.

The method may comprise the step of moving the arm datum into contact with the or each object datum by manipulating the arm through the application of external force directly to the arm.

The method may comprise, during the said moving step, automatically controlling the drivers so as to counteract the action of gravity on the arm.

According to a second aspect of the invention there is provided a robot comprising: a base; a flexible arm extending from the base and having a plurality of joints whereby the configuration of the arm can be altered; a datum carried by the arm; a plurality of drivers arranged to drive the joints to move; and a plurality of position sensors for sensing the position of each of the joints; and a control unit configured to: (i) to calculate, independence on the outputs of the position sensors when the datum carried by the arm is contacted with a first datum on an object in the environment of the robot, a distance between a reference location defined in a frame of reference local to the robot and the first object datum; and (ii) to subsequently control the drivers to reconfigure the arm in dependence on at least the calculated distance.

Instead of contacting the arm with a datum the arm may be moved into a predetermined positional relationship with the datum: for example it may be moved to a point offset by a known distance from the datum in a known direction as established, e.g. by a plurality of intersecting optical beams directed about the datum.

BRIEF DESCRIPTION OF THE DRAWINGS

The present invention will now be described by way of example with reference to the accompanying drawings, in which.

DETAILED DESCRIPTION

A surgical robot may have an arm that is flexible by virtue of a series of joints arranged along the arm which allow the arm to be reconfigured. The robot may be able to sense the configuration of its joints. When it is necessary to calibrate the robot's knowledge of its position relative to other furniture in the operating environment, for example another robot or an operating table, a first datum point on the arm can be moved into contact with a second datum point on the other furniture. By sensing the configuration of the arm when it is in contact with the second datum point the spatial relationship between the arm and the other furniture can be estimated. That relationship can then be used as data for controlling the robot during a subsequent procedure, for example to inhibit collision between the robot arm and the furniture.

Figure 1:
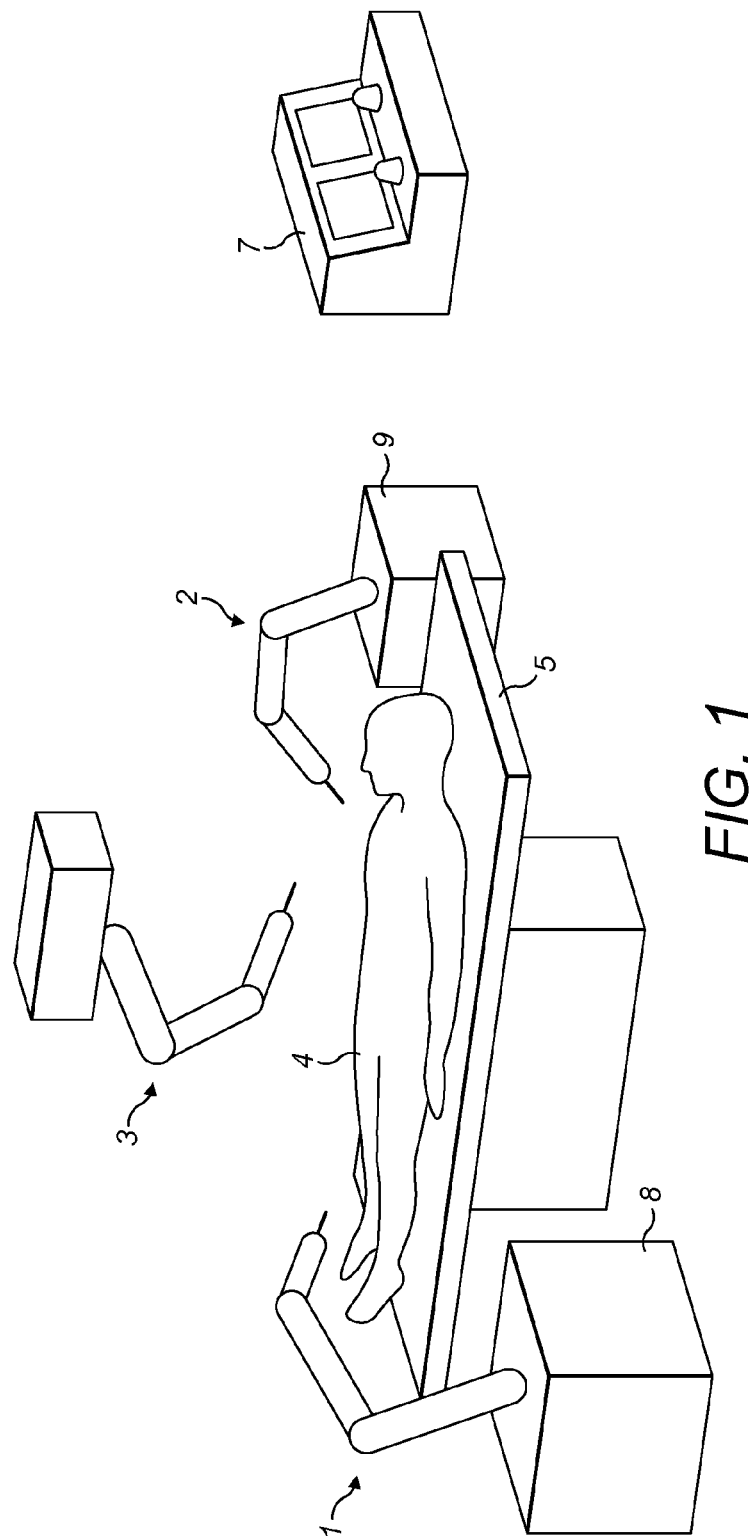
FIG. 1 shows robots positioned in readiness for performing a surgical procedure.
Figure 2:
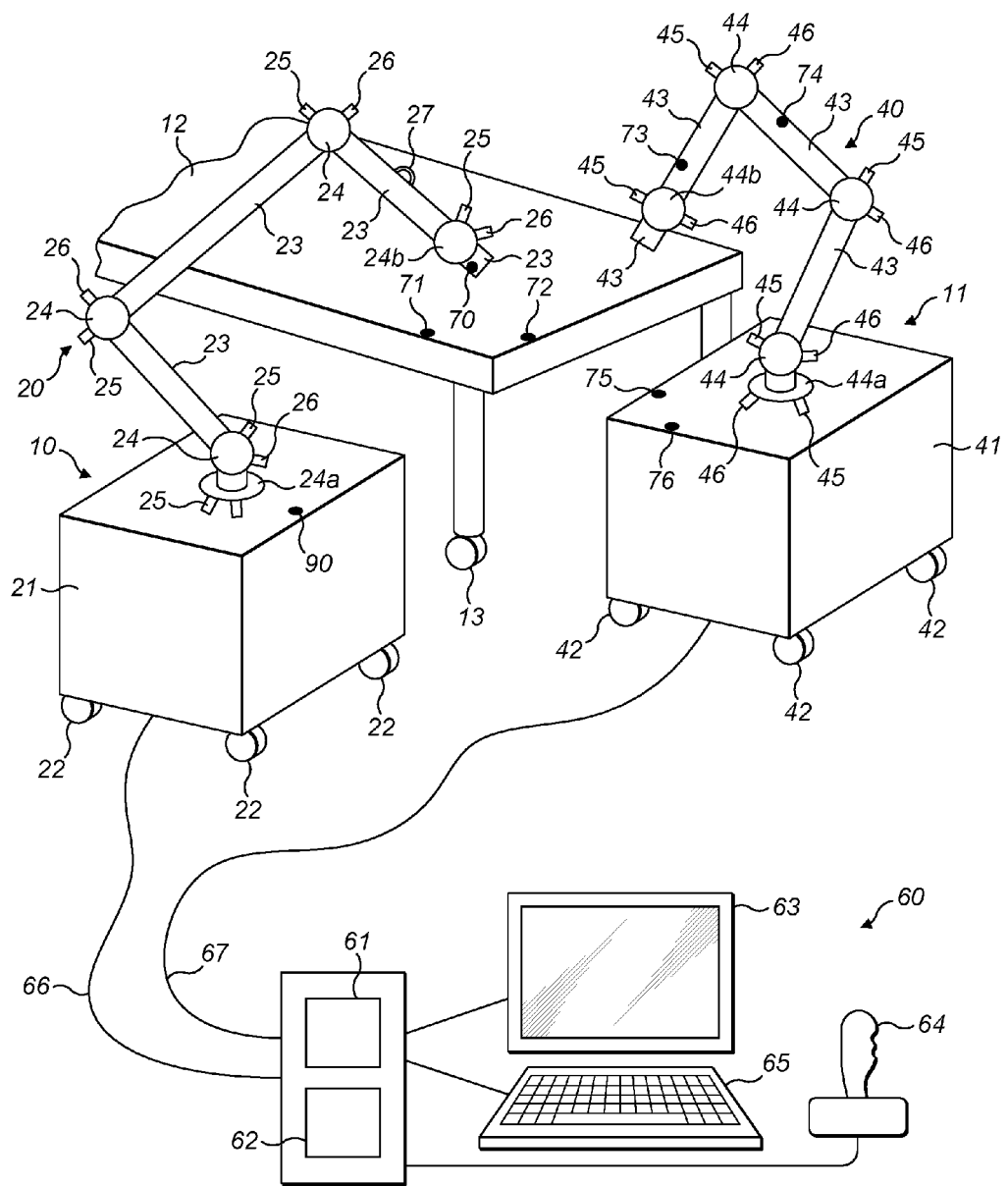
FIG. 2 shows surgical robots positioned adjacent an operating table.

FIG. 2 shows an example of a surgical environment. Robots shown generally at 10 and 11 are placed near a table 12 in preparation for performing an operation on a patient.

Robot 10 comprises an arm 20 and a base 21 in the form of a movable cart. The cart is equipped with wheels 22 by means of which it can be rolled along the floor, and brakes (not shown in the figure) which can be operated to block each wheel from rotating so as to lock the cart in place once it has been positioned appropriately. The cart itself is designed so as to have sufficient weight to provide a steady base for the robot arm without being excessively difficult to move. Robot 11 has a similar arm 40 and a similar cart 41 having wheels 42.

The table 12 is mounted on wheels 13 which also run on the floor and which can be locked by brakes.

Each robot arm has a series of rigid arm members 23, 43. The proximal arm member of each arm is joined to its base by a first revolute joint 24a, 44a. Each subsequent arm member in the series is joined to the preceding arm member by a respective revolute joint 24, 44. The final joint 24b, 44b could be a simple revolute joint, or it could be a more complex arrangement, for example as described in our co-pending application PCT/GB2014/053523. One or more of the arm joints could move linearly or with a compound motion rather than being simply rotational. The joints of each arm are configured so that collectively they provide the arm with flexibility allowing the distal end of the arm to be moved to an arbitrary point in a contiguous three-dimensional working volume. One way to achieve that is for the joints of the arm as a whole to have an arrangement as set out in PCT/GB2014/053523, for example: a most proximal joint having a substantially vertical rotation axis, a succeeding joint having a rotation axis transverse to the axis of the first joint, a succeeding joint having a rotation axis transverse to the axis of the preceding joint and extending generally between the preceding joint and the next succeeding joint, a succeeding joint having a rotation axis transverse to the axis of the preceding joint, a succeeding joint having a rotation axis transverse to the axis of the preceding joint and extending generally between the preceding joint and the next succeeding joint, a succeeding joint having a rotation axis transverse to the axis of the preceding joint, a succeeding joint having two mutually transverse rotation axes, one of which is transverse to the axis of the preceding joint, and a succeeding joint having a rotation axis transverse to the other of the axes of the preceding joint. Many other combinations and configurations of joints can be adopted, for example as are known from existing designs of industrial and other robots. There could be more or fewer joints and rigid arm members extending between them.

Each joint is equipped with an electric motor 25, 45 which is arranged so that it can cause motion of the arm about the joint. The motor could be a rotary or linear motor. Instead of electric motors the arms could be driven by other means, for example hydraulic or pneumatic actuators. Each joint is equipped with a sensor unit 26, 46 comprising a position encoder and a force transducer which can detect the configuration and the force/torque applied to the respective joint. The position sensors could, for example, be potentiometers, optical position encoders, ultrasonic or radio distance sensors. The force sensors could, for example, be resistance-based strain gauges, piezoelectric strain gauges or semiconductor strain gauges.

A control unit shown generally at 60 comprises a processor 61, a non-volatile memory 62, a display screen 63, and a user input device 64. The memory 62 stores in a non-transient way code that is executable by the processor 61 to perform the functions described herein. The control unit is communicatively coupled to the motors 25, 45 and to the sensor units 26, 46 via flexible umbilicals 66, 67 which pass to the carts. Alternatively, the control unit could communicate wirelessly with the robots. The control unit receives data from the position encoders of the sensor units. That data indicates the configuration of the arms. The control unit 60 sends signals that drive the motors 25, 45 of the arms to adjust the configuration of the arms' joints 24, 44. The outputs to drive the motors can be determined by the code running on the processor 61, optionally in dependence on inputs received from the user input device 64. In use, a surgeon can operate the user input device to signal to the processor 61 three-dimensional motions that are required of the arms. The processor can then drive the motors in response to those inputs to cause the arms to move accordingly. In that way the surgeon can control the robots to manipulate instruments borne by the robot arms in order to perform surgery on a patient. The processor receives inputs from a control panel 65, which allows the operating state of the arm to be selected. One of the robots could carry a camera. Images captured by the camera could be transmitted to the control unit 60 and displayed on the display 63 to assist the surgeon.

The code running on the processor enables motion of at least one of the arms (e.g. the arm of robot 10) to be controlled in two modes. A user can signal to the processor which mode is active at a particular time by means of the control panel 65.

In a first, driven mode the configuration of the arm is set in dependence on the inputs received from the controller 64. In this mode the operator can use the controller 64 to signal a desired configuration of the arm: for example a desired position and/or attitude of the distal end of the arm. The processor 61 determines a configuration of the joints 26 of the arm that will result in the desired configuration being achieved. Once the processor has selected a new configuration it signals the motors to cause the joints to adopt the states required to bring the arm into that configuration. In this way, in the driven mode the operator can remotely signal the robot to move the some part of the arm, for example its distal end, or the tip of a tool carried by the arm, to move to a desired location.

In a second, compliant mode the processor controls the arm to maintain a position in which it is placed by means of force applied directly to the arm. To achieve this the processor receives inputs from the position and force sensors of the sensor units 26. From the position sensors the processor knows the current configuration of the arm. The memory 62 stores for each element of the arm 20, its mass, the distance of its centre of mass from the preceding joint of the arm and the relationship between the centre of mass and the positional output of the joint sensor for the preceding joint.

Using that information the processor models the effect of gravity on the elements of the arm for the current configuration of the arm and estimates a torque due to gravity on each joint of the arm. The processor then drives the motor of each joint to apply a torque that will exactly oppose the calculated gravitational torque. With this control strategy an operator can directly push or pull any part of the arm to a desired position, and the part will stay in that position notwithstanding the effect of gravity on it and on any parts depending from it. A force on the arm may result in a torque about multiple joints. The controller can be programmed to decide to prioritise certain ones of the joints for neutralising the torque. In the compliant mode the controller may automatically control the arm to maintain a configuration imposed by an external force independently of the action of gravity, to present a limited resistance to reconfiguration under the external force independently of the action of gravity and/or to control the motors or other drivers of the arm so as to present increasing resistance to reconfiguration under the external force as the arm is moved so as to increase the deviation of the attitude of the arm relative to its base from a neutral value.

In the compliant mode some of the joints will experience no gravitational torque. The motors for those joints may be de-energised. More typically, each motor may be controlled in response to the torque measured about the respective joint. When the measured torque at a joint is adjusted for gravity any remaining torque represents a torque applied by a force due to a push on the arm or a tool carried by the arm. In response to that torque the controller may control the respective motor to move the joint in a direction so as to reduce the measured torque, and at a rate dependant on the magnitude of the measured torque, so that when an operator pushes or pulls a part of the arm the arm provides the sensation of moving freely but with some resistance in response to applied force.

In the present system at least one of the robots is capable of providing information to the control unit to characterise the surgical environment. This can be achieved by moving the arm of that robot into known spatial relationship with other objects in the environment and determining the configuration of the arm when it is in such a relationship. This process will now be described in more detail.

In one example of how the characterisation can be performed, the arm 20 of robot 10 is provided with a visible reference mark or datum 70 on its exterior surface. Each other element in the environment is provided with two such datums. Thus table 12 is provided with datums 71, 72 and the arm 55 of robot 12 is provided with datums 73, 74. A user indicates to the processor 61, for instance by means of the control panel 65, that an environmental characterisation operation is about to be performed. In response to that input the processor may automatically place the arm 35 in compliant mode. Alternatively the user may select compliant mode manually. The user then pushes the arm 35 into such a configuration that datum 70 is touching datum 71, and he provides an input to the processor to indicate that the arm is in that state. That input could be provided using the control panel 65; or using an input device 27 on the arm 20 itself. Input device 27 is more conveniently placed for a user moving the arm manually. When processor 61 receives that input it determines the configuration of the arm 20 from the position sensors at the arm's joints and from the data stored in memory 62 that defines the spacings and ranges of motion of the joints of the arm. The memory 62 also stores data defining the positional relationship of the datum 70 to the arm element on which it is located, and of the proximal joint of the arm to a reference point 90 on the base 21 of robot 10. This information allows the processor 61 to determine, when datum 70 is touching datum 71 the distance and direction from the reference point on the base of robot 10 to datum 71 on the table. The determination can be made by the processor executing code stored in memory 62 and configured to fulfil that purpose. The determined distance and direction can then be stored in memory 62. The same process is repeated for datum 72. That is: the arm 20 is manipulated so that datum 70 is touching datum 72, that state is signalled to the control unit 60, and the processor calculates and stores the distance and direction from the reference point 90 to the datum 72. The memory 62 stores data regarding the table 12: specifically its shape and size and the locations of the datums 71 and 72 on the table. With that information, once the relationships between reference point 70 and both the spaced-apart datums 71, 72 on the table have been established, the processor 61 can fully establish the orientation and distance of the table relative to the base of robot 10.

Next a similar process is performed to determine the relationship between the robots 10 and 11. Datums 73, 74 are located on the arm 40 of robot 11. The processor 61 knows the configuration of the arm of robot 11, from its position sensors, memory 62 stores the positional relationship of the datums 73 and 74 to the arm element(s) on which they are located. The operator touches datum 70 is touched to datums 73 and 74 and each time that state is signalled to the processor. With that information the processor can determine the position and distance of the base of robot 11 from the reference point 90 on robot 10.

To fully characterise the spatial relationship between a robot and another furniture item in the operating environment, the processor 61 can utilise: (i) two datum measurements, for example those described above in which a datum on the robot makes contact with each of two datums on the table; and (ii) the joint position measurements from the position sensors, which enable determination of the configuration of the robot arm; and (iii) the torque measurements from the torque sensors, which enable the direction of gravity to be determined and hence the orientation of the robot arm. All these measurements are taken when the robot arm is placed in a compliant mode to perform the characterisation as described above with respect to FIG. 2.

Alternatively, to fully characterise the spatial relationship between a robot and another furniture item in the operating environment, the processor 61 can utilise: (i) the joint position measurements from the position sensors, which enable determination of the configuration of the robot arm; and (ii) three datum measurements, for example those described above in which a datum on the robot makes contact with each of two datums on the table, which together with the joint position measurements enable the orientation of the robot arm to be determined.

Some examples of ways in which this process could be varied are as follows.

Figure 3:
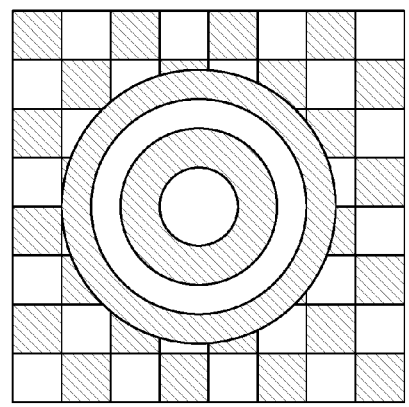
FIG. 3 shows an example of a visual target.
Figure 4:
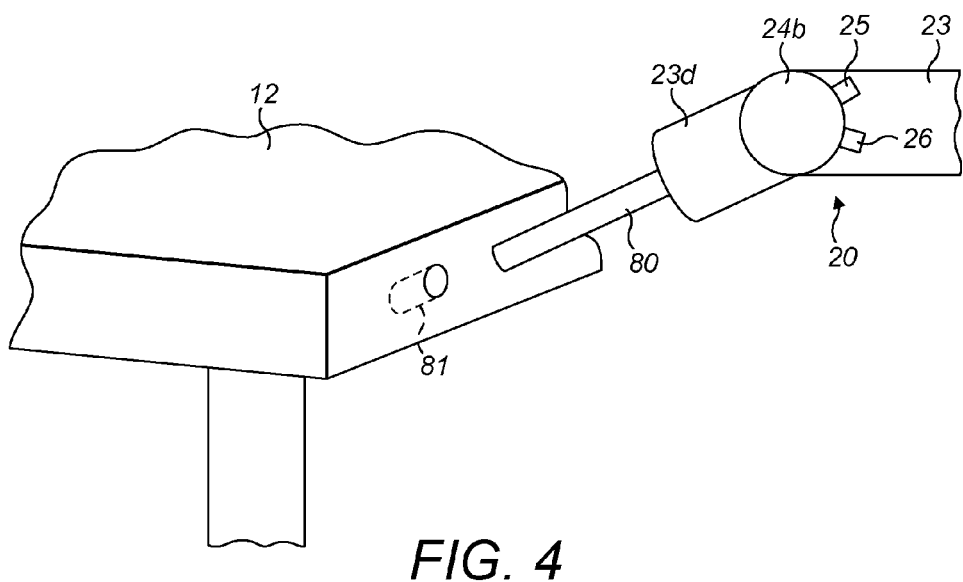
FIG. 4 shows an example of an orientational target.

1. Instead of using datums 73, 74 on the arm of robot 11, datums 75, 76 on the base of robot 11 could be used.
2. A single datum point on each robot could be touched to both datum points on the table. That would provide the processor with sufficient information to establish the relationship between the robots and the table and also to each other. Alternatively, sufficient information can be gathered to fully characterise the locations and orientations of the two robots and the table if (a) the robots are each touched to a different datum point on the table and (b) the robots are be touched together in two different relative positions. It will be appreciated that in general various different combinations are possible.
3. Similar steps could be undertaken to characterise the spatial relationship between the arms and other equipment in the surgical environment, for example additional robots, or obstacles such as additional carts carrying patient monitoring or life-support equipment.
4. Instead of moving the arm(s) in compliant mode to move the datums together, it could be done using the controller 64. Alternatively it could be done automatically. One of the robots could be equipped with a camera. Video analysis of the output of the camera could be performed to identify the datums to which the arm is to be touched, and the arm could then be controlled automatically to bring a predetermined part of that arm into contact with the datums. To assist this process the datums could be distinctive high-contrast targets, for example as illustrated in FIG. 3.
5. To avoid the need to take multiple measurements on an object in order to establish its orientation a datum could be configured to be directional, and the robot by means of which the characterisation is being performed could be contacted with the datum in an orientation governed by the datum. For example, FIG. 4 shows a datum 81 in the form of a blind socket in the table 12. In this example the arm is equipped with a male probe 80 which can mate with the socket 81 in such a way that when the probe is fully inserted into the socket both the orientation and the position of the probe is fixed relative to the socket. The memory 62 stores the relationship between the socket 81 and the remainder of the table, and the relationship between the probe 80 and the arm member 23d which carries the probe. This allows the processor 61 to determine the position and orientation of the table relative to the probing robot arm in a single step. Similar mechanical interfaces which impose a directional and positional relationship between the sensing arm and a subject could be implemented on other furniture in the surgical environment. The probe could releasably attach to an instrument interface of the robot arm, for example on the distal element of the robot arm.
6. To establish both a position and direction between two robot arms, single datums on the arms could be touched together and then held in contact as both arms are moved simultaneously.
7. The arm could be provided with a tool that bridges between two visible datum points on a subject and thereby indicates to the processor both the position and direction of the subject at the point when the tool is bridged between the points.
8. A measurement tool such as those discussed at points 4 and 7 above could be telescopic to allow it to extend to subjects that are normally out of reach of the arm to which it is fitted. The tool could have sensors measuring the length of the tool and indicating that to the control unit 60 for use in estimating the position of the subject.

The arm could comprise a communication interface such as a set of electrical connectors or a wireless transceiver for sensing what type of tool is installed on the arm. That data could be signalled to the control unit. When a tool attached to the arm is one designed for performing the characterisation procedure (e.g. tool 80 in FIG. 4, or a tool as described at points 7 and 8 above) then the control unit can automatically control the arm to enter a mode suitable for performing the characterisation procedure: for example the compliant mode.

There could be a protocol of contacting the arm(s) to the datums on the other objects in a predetermined order. Then the processor can know which datum is being sensed each time it is informed that contact is made to a datum. The control unit may instruct a user (e.g. by audible announcements) which datum to contact next. Alternatively, the user may signal (e.g. by means of the control panel 65) which datum is being contacted.

Once the processor knows the relationship between the elements in the surgical environment, that information can be used in a number of ways. For example:

There may be multiple configurations of an arm that will result in the tool tip and/or the arm's distal end being placed in a desired position. The processor 61 may select between those configurations based on an algorithm that seeks to avoid collisions between the arm and other objects known to the processor to be near the arm.

The processor may be configured to cause one arm automatically to track another, for example to cause one arm to image or irradiate a site at which the other arm is working, or to cause one arm to automatically help to support a heavy tool being used by the other, or to cause one arm to pass a supply of material such as suture thread to the other arm.

The relative locations of the arms may influence how the arms react to control inputs from a user, or how data from or about the arms is displayed to the user.

In an alternative approach, the arms of multiple robots could be displaced so that datums thereon are contacted with, a common reference datum. The spatial offset from each robot's base to the reference datum and/or the orientation of each base relative to the datum could be computed in the matter described above. Then the spatial offset between the robots' bases and/or the relative orientation of the bases can be calculated from the addition of the spatial offsets and/or orientations of the bases relative to the datum. If appropriate an offset between the locations where the robots' arms are mated to the common datum could be added. For example, the reference datum could be a fixed or mobile block having formations (e.g. sockets) to which the distal ends of multiple robot arms could be mated. If the block is mobile then when the arms are simultaneously mated to the block then the relative positions of their bases can be determined. If the block is fixed in location then the arms could be mated to the block one-by-one.

The datum may be any 1-dimensional (1D), 2-dimensional (2D) or 3-dimensional (3D) structure suitable for use in performing the characterisation as described herein. The datum described with respect to FIG. 2 is a 1D or 2D mark. The datum described with respect to FIG. 4 is a 3D formation in the shape of a socket. The datum may be directional so that the orientation of the robot arm is constrained, fixed, or otherwise dependent on the orientation of the datum when mated with it.

Figure 5:
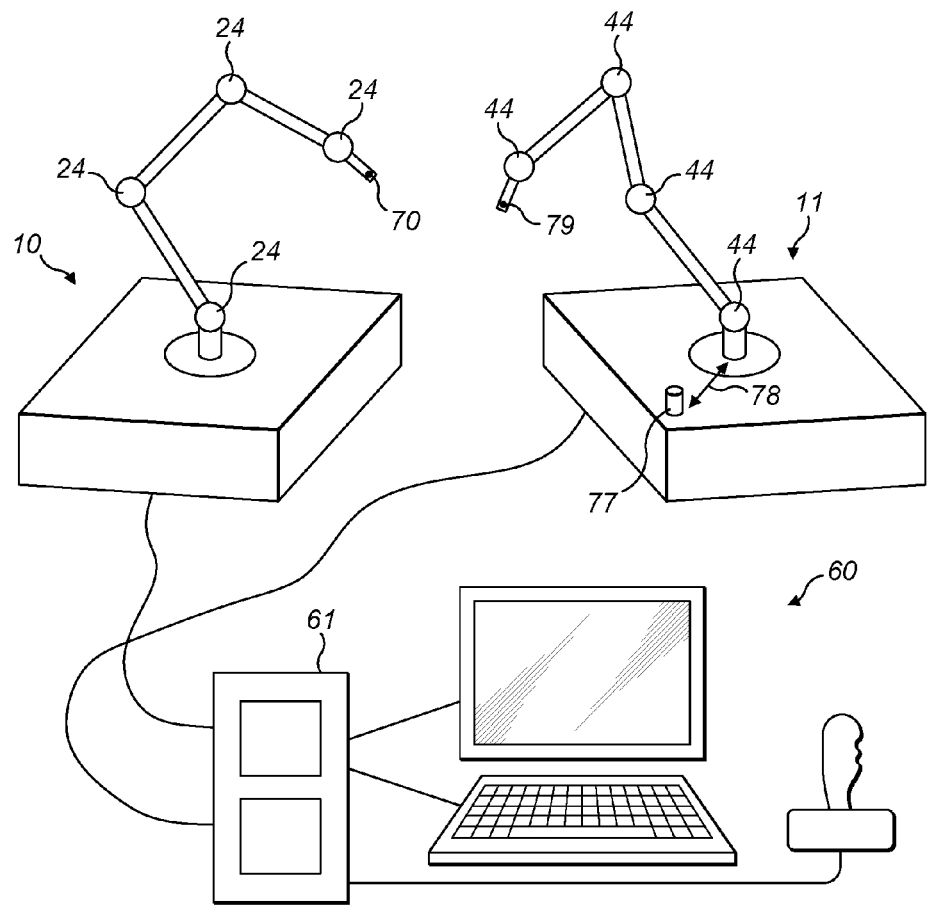
FIG. 5 shows an example of a datum located proximal to a robot.

FIG. 5 shows an example in which a robotic system utilises a datum which is a 3D formation. The robotic system comprises robots 10 and 11 as described above with respect to FIG. 2. Robots 10 and 11 are shown without instruments attached to their arms. First robot 10 comprises a first datum 70 carried on its arm. In this example, the first datum is located on the part of the first robot arm that interfaces with the instrument, herein referred to as the instrument interface. The second robot 11 comprises a second datum 79 carried on its arm. There is also a third datum 77 positioned within the environment of the first and second robots 10 and 11. The third datum 77 is proximal to the first and/or second robot. In FIG. 5, the third datum 77 is located proximal to the base of robot 11. However, as will be apparent from the following, this is merely an example and the third datum may occupy a variety of positions within the vicinity of the first and second robots.

The control circuit comprising processor 61 is denoted generally at 60.

The third datum 77 is, in this example, at a known distance from the base of the arm of the second robot 11, this distance being denoted 78. Thus the third datum 77 is at a known position with respect to the second robot 11. The distance and/or orientation of the third datum 77 with respect to the second robot 11 may be known by the processor 61. For example, the distance and/or orientation of the third datum 77 with respect to the base of the second robot 11 may be known by the processor 61. Alternatively or additionally, the position and/or distance of the third datum 77 relative to another reference point of the second robot 11 is known by the processor.

The first datum 70 and/or the part of the first robot arm on which the first datum 70 is located, and the third datum 77 are mutually configured so that when the datums 70 and 77 are mated, the configuration of the first robot arm 10 is dependent on the position and orientation of the third datum 77. In the example shown in FIG. 5, the first datum 70 is a reference mark on the instrument interface of the first robot arm. The third datum 77 is a 3D formation which may take any shape so long as the first datum 70 is only able to mate with the third datum 77 in a single position and orientation relative to the third datum 77. Thus, there is only one configuration of the part of the first robot arm on which the first datum 70 is located which is able to engage with the third datum 77. The third datum 77 may be a 3D formation which has an interface having the same shape as the part of an instrument that interfaces with the robot. In other words, the third datum 77 may be in the shape of a dummy proximal instrument end. The third datum 77 may comprise a socket configured to receive the first datum 70, as shown in FIG. 4. In this example, the socket defines a complementary space to the shape delineated by the instrument interface, or a part thereof. In all examples, when mated, the position and orientation of the first datum 70 is fixed relative to the third datum 77. Since the third datum 77 has a fixed position and orientation with respect to the second robot 11, the orientation of the first datum 70 is also fixed with respect to the second robot 11 when the first datum 70 is mated with the third datum 77.

To calibrate the position and/or orientation of the first robot 10 relative to the second robot 11, the arm of the first robot 10 is manipulated so that the first datum 70 mates with the third datum 77. The arm of the first robot 10 may be manipulated in any of the ways described above.

As described above, mating the first datum 70 with the third datum 77 constrains the orientation of the first datum 70 relative to the second robot 11. Once mated, the processor 61 measures the joint angles for each of the joints of the first robot 10 (which may be referred to as the joint states) and, using knowledge of those joint states and the length of each of the limbs of the arm, calculates the distance between the third datum 77 and a reference point (e.g. the base) of the first robot 10. Because the orientation of the first datum 70 is constrained by the third datum 77, the processor can also calculate the orientation of the first datum 70 with respect to the first robot 10 and the second robot 11. Because the processor 61 also knows the relationship between the third datum 77 and a reference point of the second robot 11 (e.g. the base of robot 11), it can calculate the position and orientation of the first robot 10 with respect to the second robot 11. For example, the processor may sum the distance and angular measurements of the third datum 77 relative to the first robot 10 with the distance and angular measurements of the third datum 77 relative to the second robot 11.

The resultant distance between first and second robots 10 and 11 may be defined with respect to a reference location of the probing robot (first robot 10). That reference location may be defined in a local frame of reference of the first robot 10. Similarly, the orientation of the second robot 11 relative to the first robot 10 may be defined relative to a reference direction defined in a frame of reference local to the first robot 10. Alternatively, the resultant distance between the first and second robots 10 and 11 may be defined with respect to a further frame of reference. The further frame of reference is different to the local frame of reference of the first robot 10 and different to the local frame of reference of the second robot 11. The further frame of reference may be the local frame of reference of an imaging device. For example, the further frame of reference may be the local frame of reference of an endoscope. The endoscope may be attached to a further robot arm.

By causing the orientation of the first datum 70 to be fixed with respect to the third datum 77 when they are mated, the position and orientation of the first datum 70 (and hence the first robot 10) can be calculated with respect to the second robot 11 in a single calibration step.

The characterisation described with respect to FIG. 5 is carried out utilising the first and second robots 10 and 11, the third datum 77 and the processor 61 only. The operating table is not required. Once the characterisation is complete, the patient may be brought into position for the operation, for example on a trolley.

Figure 9:
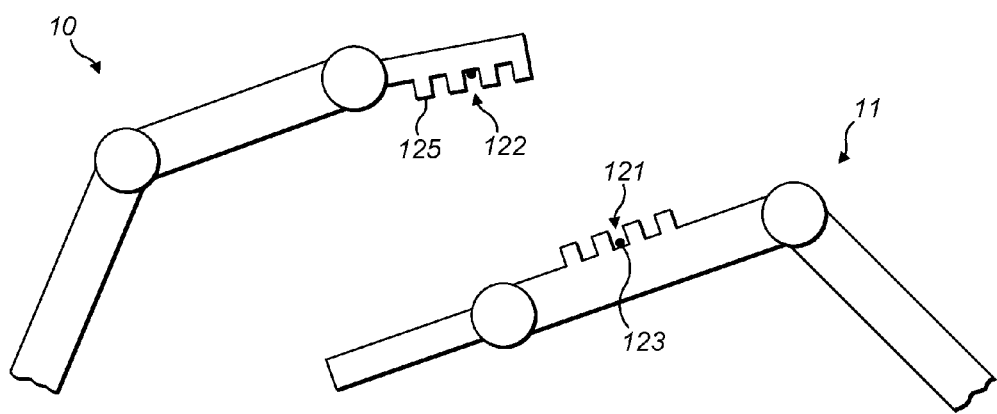
FIG. 9 shows an example of datums on the distal ends of robot arms.

FIG. 9 illustrates a further example in which a first datum 125 on the arm of the first robot 10 mates with a second datum 121 on the arm of the second robot 11. In this example, the first datum 125 is a 3D formation integral with the arm of the first robot 10. The second datum 121 is a 3D formation integral with the arm of the second robot 11. FIG. 9 just shows the ends of the arms of the first and second robots 10 and 11. The remainder of the robots has been omitted for clarity and ease of illustration. In this example, the first datum 125 defines a mating surface integral with the arm of the first robot 10. The mating surface may form part of, or otherwise be attached to, the casework of the arm of the first robot 10. The second datum 121 defines a complementary mating surface integral with the arm of the second robot 11. The complementary mating surface may form part of, or otherwise be attached to, the casework of the arm of the second robot 11. The complementary mating surface 121 is configured to be complementary in shape to, and engage, mating surface 125. The surfaces 121 and 125 may further be mutually configured so that they can mate only in one relative orientation. The mating surface 125 may be the instrument interface of first robot 10. The complementary mating surface 121 may have the same shape as the part of an instrument that interfaces with the first robot's 10 instrument interface. For example, the complementary mating surface 121 may be a dummy proximal instrument end which is attached to the casework of the arm of the second robot 11.

The first and second datums 125, 121 may each additionally comprise a reference mark 122, 123 to aid alignment of the datums.

In this way, when the first and second robot arms are brought together and the surfaces 125 and 121 mated, the orientation and distance of the first datum 125 can be calculated in a similar manner to that described above. For example, the processor 61 may exploit knowledge of the joint states of the second robot 11 when the surfaces 121 and 125 mate to calculate the distance between the second datum 121 and a reference point of the second robot 11. The joint states of the first robot 10 can then be used to calculate a distance and orientation of the first datum 125 with respect to a reference point of the first robot 10. These distances and orientations can be used to calculate the distance and relative orientation of the first and second robots 10 and 11.

In the arrangement of FIG. 9, no items additional to the robot arms are needed to perform the characterisation. Additionally, using this arrangement a further robot could more easily be calibrated mid-operation by attaching its instrument interface to the complementary mating surface 121 of the second robot 11.

As mentioned above, both robot arms may mate with a common datum. The common datum could, for example, comprise first and second interfaces having a known relationship (e.g. positional and/or orientational) to each other.

In this case, to determine the position and orientation of one robot relative to the other, a datum on the arm of each robot mates with a respective interface on the common datum. The first and second interfaces of the common datum may be configured so that when the first interface is mated with a first datum on the first robot, and the second interface is mated with a second datum on the second robot, the configurations of both robots depend on the orientation of the common datum. That is, the orientation of each robot's datum is fixed relative to the orientation of the common datum when that robot is mated with the common datum.

In this way, the processor 61 may calculate the position and orientation of the common datum with respect to the first robot 10 from the joint states of the first robot 10 when the first datum carried by the arm of the first robot 10 mates with the first interface of the common datum; and may calculate the position and orientation of the common datum with respect to the second robot 11 from the joint states of the second robot 11 when the second datum carried by the arm of the second robot 11 mates with the second interface of the common datum. Because the common datum is of known geometry (i.e. the relationship between the first and second interfaces is known), the processor can calculate the orientation of the first and second robots relative to each other by mating both the first and second datums to the common datum. The distance between the first and second robots can also be calculated from the distances between each of the first and second robots and the common datum. Suitably, the common datum is a 3D formation. This 3D formation may be referred to as a calibration object.

Both the first and second robot arms need not mate with the common datum simultaneously, or concurrently (though they may), so long as the position and orientation of the common datum is the same at the moment when each arm mates with it. Thus, the first and second robot arms may mate with the common datum during different, non-overlapping time periods. However, the position and orientation of the common datum remains constant in the time between the first robot arm mating with the common datum and the second robot arm mating with the common datum.

Figure 6A:
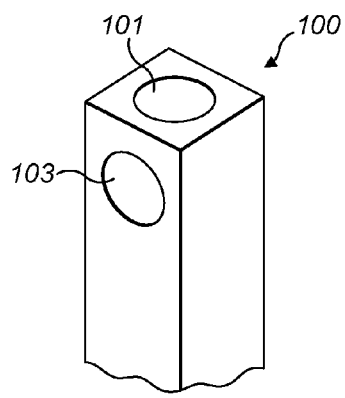
FIGS. 6a and 6b show example datums having two interfaces.

An example of a common datum is shown in FIG. 6A. The common datum 100 is a 3D formation in the shape of a block. Common datum 100 comprises first interface 101 and second interface 103. Each of the first and second interfaces is in the shape of a socket. The sockets are in a known orientation relative to each other. This orientation may be known by processor 61.

Block 100 may be fixed in position and orientation within the environment of the first and second robots 10, 11. The block 100 may be located on the base of one of the robots, or it may be remote to both robots. To calibrate the positions and orientations of the first and second robots, a first datum carried by the arm of the first robot (e.g. located on its instrument or endoscope interface) may mate with socket 103, and a second datum carried by the arm of the second robot (e.g. on its instrument or endoscope interface) may mate with socket 101. Because the processor 61 knows the relative orientations of sockets 101 and 103 it can use the joint states of both robots at the time of mating with the block 100 to calculate the relative orientation of the robots. The distance between the robots can also be calculated. As described above, that orientation may be calculated with respect to a reference direction defined in a coordinate system, or reference frame, local to one of the robots. Alternatively, the reference direction may be defined in a coordinate system, or reference frame, local to a third body, such as an endoscope. The distance between the robots may be calculated between a reference point on one of the robots and a reference point on the other of the robots. Those reference points may be the bases of the robots, for example. The distance may be calculated in a frame of reference local to one of the robots (which may be the same robot with which the orientation is defined with respect to). Alternatively, the distance may be calculated in a frame of reference local to a third body, such as an endoscope.

Figure 6B:
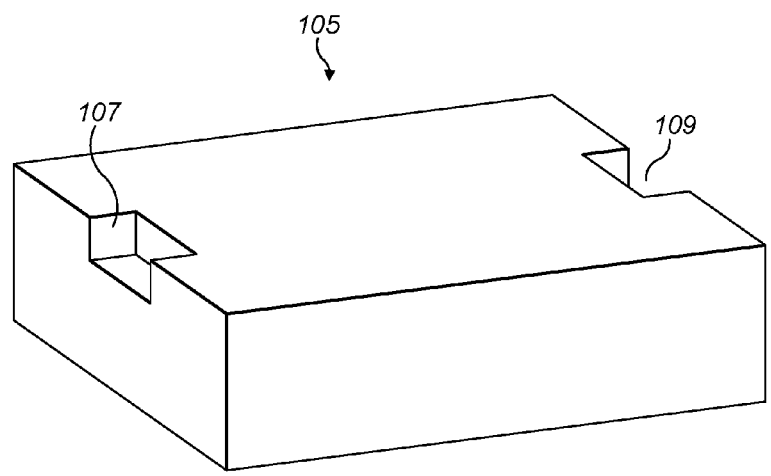

Another example of a common datum is shown in FIG. 6B. The common datum 105 is a 3D formation in the shape of a block. Common datum 105 comprises first interface 107 and second interface 109. Both interfaces are in the shape of slots in the common datum 105. The slots 107, 109 are in a known orientation relative to each other. This orientation may be known by processor 61. The relative orientation of slots 107 and 109 is different to that of sockets 103 and 101 in FIG. 6A.

The common datum may be fixed in space (as in the example of FIG. 6A), or alternatively it may be mobile. A mobile common datum does not have a fixed position within the environment of the robots. The mobile common datum is moveable relative to the first and second robots 10 and 11.

Figure 7:
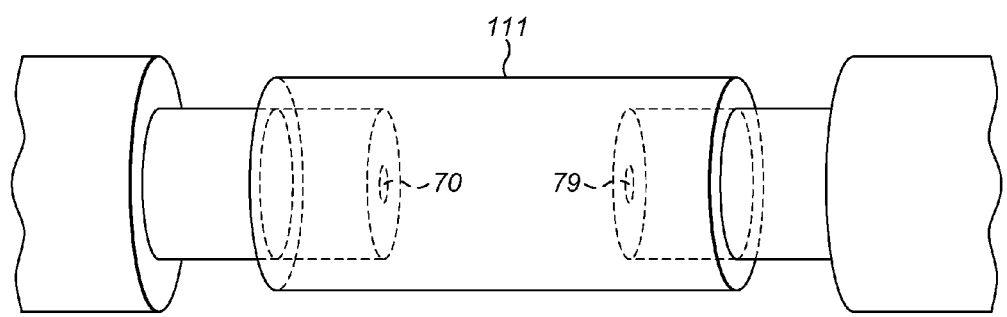
FIG. 7 shows a further example datum having two interfaces.

An example of a mobile common datum is shown in FIG. 7. The mobile common datum 111 comprises two interfaces. These interfaces are shown as sockets, although may take any suitable form. The datum 111 is shown as a block, but may take any suitable form. The geometry of the common datum 111 is known, and thus the relative orientations and positions of the sockets is known.

The terminal ends of the first and second robots 10 and 11 are also shown. The arm of the first robot 10 carries a first datum 70 and the arm of the second robot 11 carries a second datum 79.

In this example, to calculate the relative positions and orientations of the first and second robots 10 and 11, both the first and second robot arms are manipulated so that both the first and second datums 70 and 79 mate with respective sockets of the common datum 111 concurrently, or simultaneously.

The common datum 111 and the first and second arm datums 70, 79 are mutually arranged so that the joint configuration of the first robot 10 depends on the orientation of the common datum 111 when the first datum 70 is mated with one of the interfaces of the common datum 111, and the joint configuration of the second robot 11 depends on the orientation of the common datum 111 when the second datum 79 is mated with the other of the interfaces of the common datum 111. That is, the interfaces of the common datum 111 fix the orientation of the first and second datums with respect to the common datum 111 when mated. Thus, when both the first and second datums 70, 79 are mated to the common datum 111, the common datum 111 fixes the orientations of the first and second robot datums 70, 79 relative to each other.

The processor 61 calculates the distance between, and relative orientations of, the first and second robots 10 and 11 in an analogous manner to that described above with respect to the fixed common datums shown in FIGS. 6A and 6B. In summary, the processor can calculate the distance and orientation between the robots from: i) the distance from a reference point of the first robot 10 to the common datum 111, and the orientation of the common datum 111 relative to a reference direction in a frame local to the first robot 10; ii) the distance from a reference point of the second robot 11 to the common datum 111; and iii) the geometric relationship between the two interfaces of the common datum 111.

The principles described above can also be used to calibrate the positions and orientations of three or more robots. There are several ways this may be done.

Figure 8:
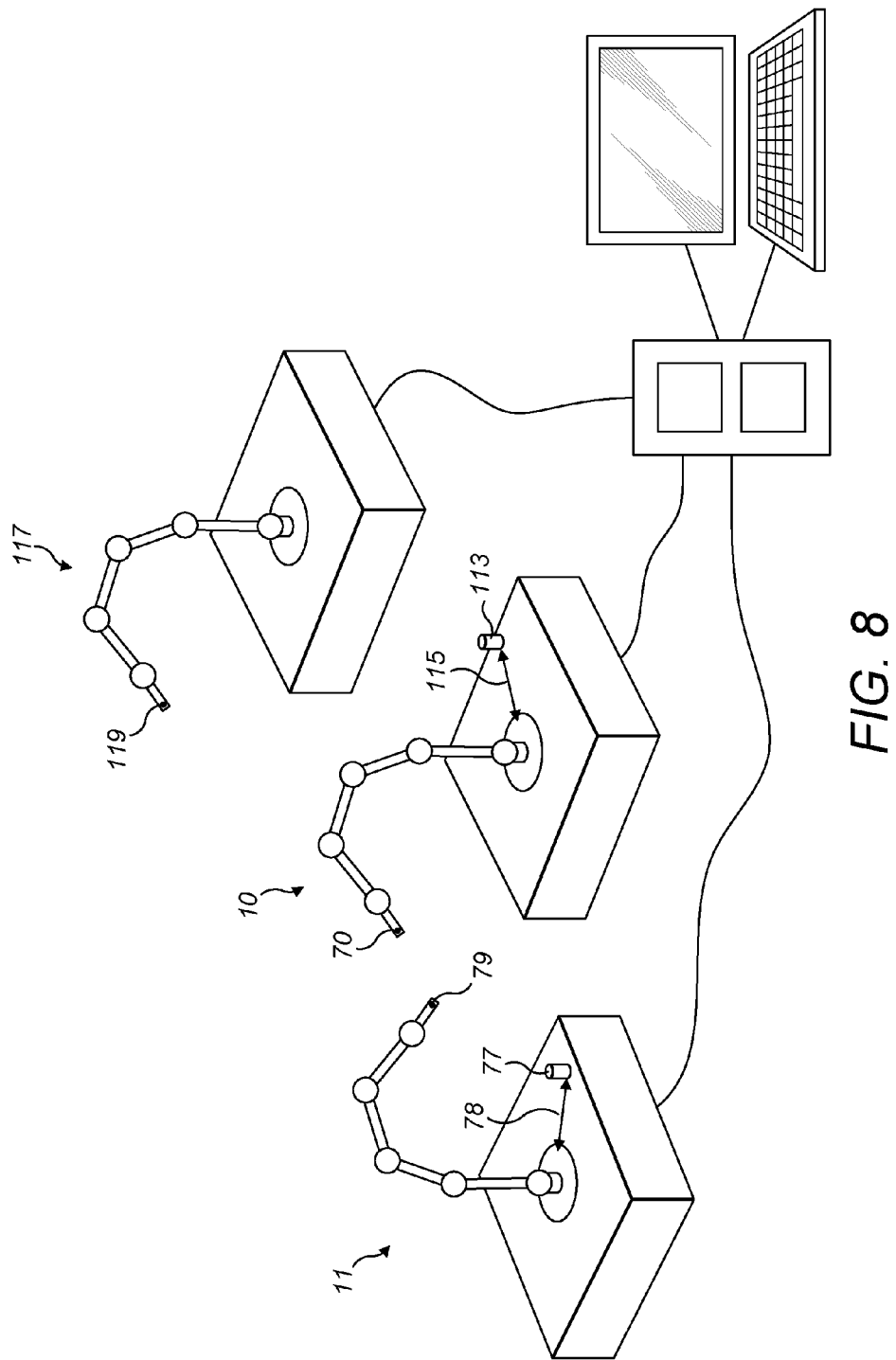
FIG. 8 shows an example of a robot system having three surgical robots, each having a datum.

One approach is illustrated in FIG. 8 and involves sequentially calibrating each of the robots with respect to each other so that each robot is calibrated with respect to a reference robot.

The robotic system comprises three robots: a first robot 10, a second robot 11 and a third robot 117. The first robot 10 comprises a first datum 70 carried by its arm. The second robot 11 comprises a second datum 79 carried by its arm and a third datum 77 having a known relationship to the second robot 11. The third robot 117 comprises a fourth datum 119 carried by its arm. The first robot 10 further comprises a fifth datum 113 in the vicinity of the first robot 10 and having a known relationship to the first robot 10. For example, the fifth datum 113 may be located proximal to the base of the first robot 10.

In this example the third datum 77 and the fifth datum 113 are in the form of fixed blocks, each having a single interface in the form of a socket. The first datum 70 and the fourth datum 119 may be attached to or form part of the instrument interface, or endoscope interface, of their respective robots. In that case blocks 77 and 113 may be shaped so as to simulate the proximal end of an instrument/endoscope.

A control circuit 60 comprising processor 61 is also shown coupled to each robot.

The steps of how the robots are calibrated will now be described.

As a first step, the first datum 70 carried by the arm of the first robot 10 is mated with the third datum 77 attached to the base of the second robot 11. The orientation of the first datum 70 is fixed with respect to the third datum 77 when mated to it. Thus, the processor 61 can determine, from the joint states of the first robot 10 measured at the time the first datum 70 is mated with the third datum 77, the orientation of the third datum 77 with respect to a reference direction and the distance from a reference position on the first robot 10 to the third datum 77. Because the relationship of the third datum 77 to the second robot 11 is also known, the position and orientation of the first robot 10 relative to the second robot 11 can be determined. In this instance, the second robot 11 may be referred to as the reference, or primary robot.

Next, the fourth datum 119 carried by the arm of the third robot 117 is mated with the fifth datum 113 attached to the base of the first robot 10. The configuration of the third robot 117 is dependent on the orientation of the fifth datum 113 when the fourth datum 119 is mated to it, and thus the joint states of the third robot 117 when the fourth datum 119 mates with the fifth datum 113 can be used to determine the distance and orientation of a reference point on the third robot 117 to the fifth datum 113. Because the relationship between the fifth datum 113 and the first robot 10 is known, the distance and orientation between the third and first robots 117 and 10 can be calculated.

Thus the relationship between robots 117 and 10 can be determined, thereby also enabling the relationship between robots 117 and 11 to be determined based on the previously calculated relationship between robots 10 and 11.

Alternatively, each of the robots may be calibrated sequentially using a datum in the form of a mobile block (e.g. as shown in FIG. 7). In this case, the first and second robots 10 and 11 may be manipulated so that the first and second datums 70 and 79 are mated to a common mobile datum 111 concurrently. This enables the relationship between the first and second robots 10 and 11 to be calculated by the control system as described above with respect to FIG. 7.

Once this has been done, the first and third robots 10 and 117 are manipulated so that the first and fourth datums 70 and 119 are mated to the common mobile datum 111 concurrently. This then enables the relationship between the first and third robots 10 and 117 to be calculated.

Because the relationship between the first and second robots 10 and 11 is known, and the relationship between the first and third robots 10 and 117 is known, the relationship between the second and third robots 11 and 117 can be calculated. Thus the relationship of each robot relative to the second robot 11 may be determined sequentially. In this regard, the second robot 11 may be referred to as a primary, or reference robot.

It will be appreciated that in both of these examples any suitable number of robots (e.g. four or more) can be calibrated in a similar manner.

The examples described above enable each robot to be calibrated relative to a reference robot by daisy-chaining the calibrations. In another set of examples, three (or more) robots can be calibrated in one calibration step by concurrently, or simultaneously, mating each of their datums with a common datum.

For example, the datum may be in the form of a unit, or block having three (or more) interfaces for mating with datums carried by respective robot arms. The block may be in a similar form to that shown in FIG. 7, but instead may comprise three (or more) interfaces having a known geometry, or relationship. The interfaces of the block may all be the same, or they may be different. For example, two of the interfaces may be configured for mutual engagement with an instrument interface of a robot arm, and the other interface may be configured for mutual engagement with an endoscope interface of a robot arm (e.g. if the datum carried by one of the arms is located on the endoscope interface).

Once the three (or more) datums of the robot arms are concurrently mated with the common datum, the relative distances (and orientations) of the three (or more) robots may be calculated. This is because the common datum and the arm datums may be mutually configured so that, when mated, the orientations of the arm datums are fixed relative to the common datum and thus relative to each other.

In an exemplary arrangement, a plurality of robots (e.g. three or more) may be mounted in sockets on a common chassis. The chassis may be a cart.

Such a robotic system may be configured so that the spatial relationship between the robot sockets is known (e.g. by control system 60). This arrangement enables the relationship of all the robots to each other to be established with a single calibration step by exploiting knowledge of the spatial arrangement of the sockets.

For example, if the chassis contains four sockets with a respective robot seated in each socket, then once one of the robots has been calibrated relative to another (e.g. using any of the methods described herein), then the relationship between all of the other robots can be known from the knowledge of the spatial relationship of the sockets.

To do this, the control system may need to know which robot is in which socket. One way of doing this is to associate an ID with each socket (e.g. 1, 2, 3, 4 etc.) and an ID with each robot (e.g. A, B, C, D etc.). These IDs may be pre-allocated or may be allocated on the fly during the set-up procedure.

In this way, when one robot is calibrated relative to another, the control system can use the IDs of the sockets those two robots are seated in. The control system can then locate the remaining robots by associating the IDs of those robots with the corresponding socket IDs and using its knowledge of the spatial arrangement of those sockets relative to the sockets of the calibrated robots.

The principles described above are applicable to other types of surgical robot than the ones shown in FIGS. 2, 7 and 8. For example, the base of the robot could be floor-mounted, ceiling-mounted or mounted to a bed or table. The joints and members of the robot arm could be provided in any suitable way. The terminal element of the robot could be provided with a sliding rail by means of which the tool can be inserted into a patient. The robot could be for purposes other than surgery. For example, it could be used for industrial manufacturing, testing or assembly.

When the relative positions of the datums are being detected the motors of the arm(s) could be inactive, so they do not even oppose gravity. If the arm were entirely flexible then the force sensors could be omitted. However, this might make it more difficult for the operator to manipulate the arm.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A method of characterising the environment of a first robot, the first robot having a base, a flexible arm extending from the base and having a plurality of joints whereby the configuration of the arm can be altered, a first datum carried by the arm, a plurality of drivers arranged to drive the joints to move and a plurality of position sensors configured to sense the position of each of the joints, the method comprising:

mating the first datum carried by the arm of the first robot with a second datum on a second robot in the environment of the first robot, wherein the second robot has a base, a flexible arm extending from the base and having a plurality of joints whereby the configuration of the arm can be altered, and a plurality of drivers arranged to drive those joints to move, and the datum carried by the arm of the first robot and the datum on the second robot are mutually configured so that the configuration of the first robot arm is dependent on the orientation of the second datum when the datums are mated;

calculating in dependence on the outputs of the position sensors when the first and second datums are mated a distance between a reference location defined in a frame of reference local to the first robot and the second robot and an orientation of the first robot relative to the second robot; and controlling the drivers to reconfigure the first arm in dependence on at least the calculated distance and orientation.

2. A method as claimed in claim 1, wherein the second datum is on an object on the second robot, and the step of calculating the orientation of the first robot relative to the second robot comprises calculating in dependence on the outputs of the position sensors when the first datum and the second datum are mated an orientation of the second datum relative to a reference direction defined in a frame of reference local to the first robot.

3. A method as claimed in claim 1, wherein the step of calculating is performed in dependence on stored information defining the lengths of the parts of the first robot arm separated by the joints.

4. A method as claimed in claim 1, wherein the step of controlling is performed in dependence on stored information defining the shape of the object.

5. A method as claimed in claim 1, wherein the first and second robots are surgical robots.

6. A method as claimed in claim 1, wherein the step of controlling the drivers to reconfigure the first robot arms in dependence on the calculated distance and/or orientation comprises controlling the drivers so as to inhibit collision between each arm in dependence on the calculated distance and orientation.

7. A method as claimed in claim 1, comprising the step of moving the first datum into contact with the second datum by manipulating the first robot arm through the application of external force directly to that arm.

8. A method as claimed in claim 7, comprising, during the said moving step, automatically controlling the drivers so as to counteract the action of gravity on the first robot arm.

9. A robotic system comprising:
a first and second robot, each comprising:
a base;
a flexible arm extending from the base and having a plurality of joints whereby the configuration of the arm can be altered;
a plurality of drivers arranged to drive the joints to move; and
a plurality of position sensors configured to sense the position of each of the joints;
wherein the first robot further comprises a first datum carried by its arm and the second robot comprises a second datum, the first and second datums being mutually configured so that the configuration of the first robot arm is dependent on the orientation of the second datum when the datums are mated; and
wherein the first robot further comprises a control unit configured to: (i) calculate, in dependence on the outputs of the position sensors when the first datum carried by the arm of the first robot is mated with the second datum on the second robot, a distance between a reference location defined in a frame of reference local to the first robot and the second robot and an orientation of the first robot relative to the second robot; and (ii) subsequently control the drivers to reconfigure the first arm in dependence on at least the calculated distance and orientation.

10. A method of characterising the environment of a first and second robot, each of the robots having a base, a flexible arm extending from the base and having a plurality of joints whereby the configuration of the arm can be altered, a plurality of drivers arranged to drive the joints to move and a plurality of sensors configured to sense the positions of each of the joints, wherein the arm of the first robot comprises an interface carrying a first datum, the method comprising:
mating the first datum carried by the interface of the first robot with an interface in the shape of a proximal instrument or endoscope end of a second datum in the environment of the first and second robots, the first datum of the first robot and the second datum being mutually configured so that when the first datum and the second datum are mated the orientation of the first datum is fixed with respect to the orientation of the second datum and the second datum has a known relationship to the second robot arm;
calculating, in dependence on the outputs of the position sensors of the first robot arm when the first datum and the second datum are mated, an orientation and position of the second robot relative to the first robot; and
controlling the drivers to reconfigure at least one of the first and second robot arms in dependence on at least the calculated orientation and/or position.

11. A method as claimed in claim 10, wherein the orientation and distance between the first robot and second robot is calculated in dependence on the outputs of the position sensors of the first robot arm when the first datum and the second datum are mated and the known relationship of the second datum to the second robot arm.

12. A method as claimed in claim 10, wherein the second datum is located on the second robot.

13. A method as claimed in claim 10, wherein the arm of the second robot carries a third datum and the second datum comprises first and second interfaces configured to mate with the first and third datums, the first interface having a known relationship to the second interface, the method further comprising:
mating the first datum with the first interface of the second datum;
mating the third datum with the second interface of the second datum when the second datum is in the same position and orientation as when the first interface was mated with the first datum; and
calculating, in dependence on: i) the outputs of the position sensors of the first robot arm when the first datum and first interface are mated; and ii) the outputs of the position sensors of the second robot arm when the third datum and second interface are mated, an orientation and distance between the first and second robot.

14. A method as claimed in claim 10, wherein the second datum has a fixed position and orientation in the environment.

15. A method as claimed in claim 13, wherein the second datum is a mobile block and the first and third datums are mated to the respective first and second interfaces concurrently.

16. A method as claimed in claim 10, wherein the second datum is in the form of a mating surface configured to engage a complementary surface integral with the first robot arm.

17. A method as claimed in claim 10, wherein the method further comprises characterising the environment of a third robot, the third robot comprising a base, a flexible arm extending from the base and having a plurality of joints whereby the configuration of the arm can be altered, a plurality of drivers arranged to drive the joints to move and a plurality of sensors configured to sense the positions of each of the joints, wherein the arm of the third robot carries a fourth datum; the method further comprising:
- mating the fourth datum with an object datum in the environment of the first robot, the fourth datum and the object datum in the environment of the first robot being mutually configured so that when the fourth datum and the object datum in the environment of the first robot are mated the configuration of the third robot arm is dependent on the orientation of said object datum and said object datum has a known relationship to the first robot arm;
- calculating, in dependence on the outputs of the position sensors of the third robot arm when the fourth datum and the object datum in the environment of the first robot are mated, an orientation and distance between the first robot and the third robot; and
- controlling the drivers to reconfigure at least one of the first and third robot arms in dependence on at least the calculated orientation and/or distance.

18. A method as claimed in claim 17, wherein the method further comprises calculating an orientation and distance between the third robot and second robot in dependence on the calculated orientations and distances between the first and second robots and the third and first robots.

19. A method as claimed in claim 17, wherein the object in the environment of the first robot is located on the first robot.

* * * * *

UNITED STATES PATENT AND TRADEMARK OFFICE
CERTIFICATE OF CORRECTION

PATENT NO. : 9,943,964 B2
APPLICATION NO. : 15/166449
DATED : April 17, 2018
INVENTOR(S) : Luke David Ronald Hares Page 1 of 1

It is certified that error appears in the above-identified patent and that said Letters Patent is hereby corrected as shown below:

On the Title Page

Assignee: "CMR Surgical Limited, Cambridge, MA (US)" should be -- CMR Surgical Limited, Cambridge (GB) --

Signed and Sealed this
Twenty-ninth Day of May, 2018

Andrei Iancu
*Director of the United States Patent and Trademark Office*